US00RE38522E

(19) United States
(12) Reissued Patent
Gertzman et al.

(10) Patent Number: US RE38,522 E
(45) Date of Reissued Patent: May 25, 2004

(54) MALLEABLE PASTE FOR FILLING BONE DEFECTS

(75) Inventors: Arthur A. Gertzman, West Milford, NJ (US); Moon Hae Sunwoo, Old Tappan, NJ (US)

(73) Assignee: Musculoskeletal Transplant Foundation, Edison, NJ (US)

(21) Appl. No.: 10/084,090

(22) Filed: Feb. 28, 2002

Related U.S. Patent Documents

Reissue of:
(64) Patent No.: 6,030,635
Issued: Feb. 29, 2000
Appl. No.: 09/031,750
Filed: Feb. 27, 1998

(51) Int. Cl.[7] ..... A61K 25/00; A61K 15/64; A61K 35/32
(52) U.S. Cl. ..... 424/423; 424/426
(58) Field of Search ..... 424/400, 401, 424/422, 423, 426, 489

(56) References Cited

U.S. PATENT DOCUMENTS

| | | | | |
|---|---|---|---|---|
| 2,621,145 A | * | 12/1952 | Sano | 424/423 |
| 2,968,593 A | * | 1/1961 | Rapkin | 424/549 |
| 4,172,128 A | * | 10/1979 | Thiele et al. | 424/549 |
| 4,191,747 A | * | 3/1980 | Scheicher | 424/94.62 |
| 4,595,713 A | * | 6/1986 | St. John | 523/105 |
| 4,610,692 A | * | 9/1986 | Eitenmuller et al. | 424/422 |
| 4,619,995 A | * | 10/1986 | Hayes | 536/20 |
| 4,637,931 A | * | 1/1987 | Schmitz | 424/426 |
| 5,073,373 A | * | 12/1991 | O'Leary et al. | 424/422 |
| 5,290,558 A | * | 3/1994 | O'Leary et al. | 424/422 |
| 5,314,476 A | * | 5/1994 | Prewett et al. | 623/23.63 |
| 5,356,629 A | * | 10/1994 | Sander et al. | 424/422 |
| 5,507,813 A | * | 4/1996 | Dowd et al. | 623/23.63 |
| 5,516,532 A | | 5/1996 | Atala et al. | |
| 5,707,962 A | * | 1/1998 | Chen et al. | 514/12 |
| 5,830,493 A | * | 11/1998 | Yokota et al. | 424/426 |

FOREIGN PATENT DOCUMENTS

| | | |
|---|---|---|
| EP | 0 522569 A1 | 1/1993 |
| EP | 0 784985 A1 | 7/1997 |
| WO | WO 98/14222 | 4/1998 |
| WO | WO 99/11298 | 3/1999 |
| WO | WO 99/52572 | 10/1999 |

OTHER PUBLICATIONS

D. Cram and G. Hammond, The Carbohydrates II, pp. 43–55.*

M. Iwata and M. Urist, Protein Polysaccharide of Bone Morphogenetic Matrix, "Clinical Orthopaedics and Related Research, N 87", pp. 257–273 (Sep. 1972).*

Klokkevoid et al, Osteogenesis Enhanced by Chitosan (Poly–N–Acetyl Glucosaminoglycan) in Vitro Periodontol (1996) 67:1170 1175.*

Sasaki et al., Stimulation of Osteroinduction in Bone Wound Healing by High–Molecular Hyaluronic Acid Bone, vol. 16. No. 1 Jan. 1995.*

Pillioni et al, Low Molecular Weight Hyaluronic Acid Increases Osterogenesis in Vitro, 1992, J. Dent. Res. 71 (IADR Abstracts).*

Leonard R. Rubin, M.D., F.A.C.S., *Biomaterials in Reconstructive Surgery*, p. 314 (1983).

* cited by examiner

*Primary Examiner*—Thurman K. Page
*Assistant Examiner*—Charesse Evans
(74) *Attorney, Agent, or Firm*—John S. Hale; Gipple & Hale

(57) ABSTRACT

The invention is directed toward a malleable bone putty and a flowable gel composition for application to a bone defect site to promote new bone growth at the site which comprises a new bone growth inducing compound of demineralized lyophilized allograft bone powder. The bone powder has a particle size ranging from about 100 to about 850 microns and is mixed in a high molecular weight hydrogel carrier, the hydrogel component of the carrier ranging from about 0.3 to 3.0% of the composition and having a molecular weight of about at least 10,000 Daltons. The composition contains about 25% to about 40% bone powder and can be additionally provided with BMP's and a sodium phosphate buffer.

28 Claims, No Drawings

MALLEABLE PASTE FOR FILLING BONE DEFECTS

Matter enclosed in heavy brackets [ ] appears in the original patent but forms no part of this reissue specification; matter printed in italics indicates the additions made by reissue.

FIELD OF INVENTION

The present invention is generally directed toward a surgical bone product and more specifically is a flowable gel and a malleable putty based on demineralized allograft bone particles mixed in a fluid carrier comprising a high molecular weight viscous excipient derived from the class of biomaterials known as hydrogels.

BACKGROUND OF THE INVENTION

Malleable putty is used to correct surgical defects that may be caused by trauma, pathological disease, surgical intervention or other situations where defects need to be managed in osseous surgery. It is important to have the defect filler in the form of a stable, viscous putty to facilitate the placement of the bone growth medium into the surgical site which is usually uneven in shape and depth. The surgeon will take the putty on a spatula or other instrument and trowel it into the site or take it in his/her fingers to shape the bone inducing material into the proper configuration to fit the site being corrected.

Many products exist to treat this surgical need. One example is autologous bone particles or segments recovered from the patient. When removed from the patient, it is wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. These inorganic materials are osteoconductive but are bioinert and do not absorb or become remodeled into natural bone. They consequently remain in place indefinitely as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have such as blood type compatibility, possibility of transmission of disease and unknown concentration of BMP which are to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100 ml (0.1%) and polysaccharides such as hexose and glucosamine at approximately 0.1%. Glucuronic acid is also present at approximately 0.4–1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste or gel which will promote optimum bone replacement growth, not be carried away by the body fluids at the operation site or simply fall out of the bone defect site. In an attempt to solve these and other problems, there have been a number of other attempts using other alternative mixtures and compositions.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel. GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material to be "runny" and to flow away from the site almost immediately after placement; this prevents the proper retention of the bone within the site as carefully placed by the surgeon.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier. The larger particles of demineralized bone may also retard the development of new bone by the patient because the large bony lamellae do not pack as well as the smaller grainy particles of bone. This will leave more open space and could lengthen the tine required to grow new bone and properly fill the defect. Another deficiency of using the bone lamellae is that the ends of the bony fragments are uneven and when packed into the surgical defect, leave uneven filaments of bone protruding out from the defect which can compromise the healing rate.

U.S. Pat. No. 5,290,558 discloses a flowable demineralized bone powder composition using a osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813 and the tissue forms described in these patents are known commercially as the GRAFTON Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues. Furthermore glycerol has been reported to be specifically neurotoxic and this problem is compounded when the concentration of glycerol is at the 20–95% level as disclosed in the U.S. Pat. No. 5,073,373 patent.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35 C. and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 4,191,747 teaches a bone defect treatment with coarsely ground, denatured bone meal freed from fat and ground into powder. The bone meal is mixed with a polysaccharide in a solution of saline and applied to the bone defect site.

Another prior art product is the formulation of demineralized allograft bone particles in collagen. Both bovine and human collagen have been used for this application. Bovine collagen carries the risk of an immunogenic reaction by the recipient patient Recently, it has been found that a disease of cattle, bovine spongioform encephalopathy (BSE) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

Accordingly, the prior art as embodied in the glycerol and other carrier base technology to deliver demineralized allograft bone to a surgical osseous site is replete with problems and only partially addresses the problems inherent in the correcting surgical defects.

SUMMARY OF THE INVENTION

A bone putty with a useful bulk viscosity has been achieved by using a very high molecular weight class of soluble biomaterial, hydrogel. The use of high molecular weight hydrogels preferably over one million Daltons allows the achievement of a very malleable bone putty with only 1–3% concentration of the hydrogel in the carrier. The balance of the carrier formulation is a sterile saline or pure water which avoids the toxic problems with the high concentrations of the low molecular weight organic solvents of the prior art.

It can thus be seen that the prior art has attempted to replicate putty/gel obtained by the mixing of blood with bone particles without the necessity of mixing the two together at the surgical site in non-controlled proportions and under time and space prohibitions.

The selection of high molecular weight hydrogels allows the use of the preferred small particle size granules of demineralized allograft bone. These small particles pack better in the wound defect and absorb more quickly thereby allowing the bone defect to be remodeled into the natural bone of the patient.

It is an object of the invention to utilize demineralized powdered bone in a particle size that is useful to achieve the malleability characteristics that maximizes the amount of bone in the formulation without creating a gritty, less malleable characteristic.

It is yet another object of the invention to use a calcium salt with the demineralized bone composition to aid in healing at the bone defect site.

It is an additional object of the invention to use a non toxic carrier for the bone particles which will not adversely impact on the patient.

It is another object of the invention to provide a premixed bone putty/gel in an oxygen protected carrier to keep the putty/gel from drying out or being degraded.

It is also an object of the invention to create a bone defect material which can be easily handled by the physician and does not degenerate when contacting blood flow at the surgical site.

DESCRIPTION OF THE INVENTION

The present invention is directed towards a demineralized bone powder composition to heal bone defects. The preferred embodiment of Examples I and VIII are the best mode for the putty composition and Examples XV or XVI for the gel composition. These and other alternate embodiments of the invention overcome the two basic deficiencies of the glycerol carrier and bone particle flowable compositions used in the prior art: first, the low molecular weight of glycerol; and second, the use of large particle or lamellae to achieve the preferred bulk viscosity. The types of demineralized bone used in the invention are cortical and cortico-cancellous bone powder.

Surprisingly, the combination of the 100–420 micron particle size of demineralized, lyophilized, allograft bone when mixed with very low concentrations of these very high molecular weight hydrogels in a suitable carrier produces a malleable putty with clinically useful bone inducing properties. The malleable property permits the surgeon to shape the quantity of bone putty or gel to exactly fit the surgical defect. Manipulation of the "lump" of bone putty may be done without it sticking to the gloves of the surgeon, behaving somewhat like a wet clay used in sculpting.

The ideal carriers for the malleable putty are preferably taken from high molecular weight hydrogels such as 1) Sodium Hyaluronate about $7.0\times10^5$–$3.0\times10^6$ Daltons; 2) Chitosan about $1.0\times10^5$–$3.0\times10^5$ Daltons; 3) Dextran about $1.0\times10^3$–$1.0\times10^5$ Daltons; *and* 4) Pluronics about $7.0\times10^3$–$1.8\times10^4$ Daltons[; and 5) N,O-carboxymethylchitosan glucosamine (NOCC) which is an example of the class of hydrogels known as glycosaminoglycan, a hydrogel derivative about $2.0\times10^6$–$3.0\times10^6$ Daltons].

The molecular weight of the hydrogels used in the carriers set forth in the Examples I–XVII are: Hyaluronic acid—($1.2\times10^6$ Daltons). Chitosan—($2.0\times10^5$ Daltons). Dextran (40,000 Daltons, used in example VII) or the Pluronic block copolymers of polyethylene oxide and polypropylene oxide; Pluronic® F127 - 9849 to 14,600 Daltons (avg. mol. wt.: 12,600 Daltons); Pluronic® F108–12,700 to 17,400 Daltons (avg. mol. wt.: 14,600 Daltons).

Demineralized, lyophilized allograft bone of particle size of about 100 to about 420 microns at a concentration of about 30% to 35% w/w is mixed into an isotonic saline solution of 2% hyaluronic acid of an average molecular weight of about 1.2 million Daltons and produces a highly desirable malleable bone putty. Hyaluronic acid is generally described as an acid mucopolysaccharide. It is envisioned that suitable amounts of bone morphogenic proteins (BMP) can be added to either the gel or putty at any stage in the mixing process to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However the amount of BMP varies in the bone depending on the age of the bone donor and the bone processing. Sterilization is an additional problem is processing human bone for medical use as boiling, autoclaving and irradiation over 2.0 mrads is sufficient to destroy or alter the BMP present in the bone matrix.

Another embodiment of the invention is to induce the presence of soluble calcium at the bone defect site. This will encourage new bone growth through the normal biochemical mechanism. Soluble calcium can be attracted to the surgical site by using a sodium phosphate buffer of pH 7.2 in lieu of the isotonic saline. The phosphate buffer will attract calcium cations to the site from the surrounding healthy bone and create an equilibrium concentration of the calcium precisely at the site of healing where it is most desirable to grow new bone.

Another embodiment of the invention is to create a sponge sheet or sponge mat of bone which is flexible and can be cut to shape by the surgeon. This can be made by using a cross linked hydrogel, either hyaluronic acid or chitosan and suspending a high concentration of bone particles ranging from 250–850 microns in size with up to 75% bone by weight. This is then lyophilized or freeze dried to remove the water component via ice sublimation leaving behind a flexible sheet of bone suspended in the dehydrated hydrogel matrix.

Any number of medically useful substances can be used in the invention by adding the substances to the composition at any steps in the mixing process or directly to the final composition. Such substances include collagen and insoluble collagen derivatives, hydroxy apatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin. It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growth factor (IGF-1): growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

The invention can best be understood by the following examples with the percentages being determined by weight. All examples could also be done in an aseptic environment to maintain a sterile final product.

EXAMPLES OF THE INVENTION

Example I:

A malleable putty of 2% solution Hyaluronic Acid in isotonic saline with 250–420 micron cortical allograft bone powder @30%.

502 milligrams of freeze dried cortical allograft bone of particle size ranging from 250–420 microns was mixed into 1,170 milligrams of a 2% solution of sodium hyaluronate in isotonic saline. The bone component is added to achieve a bone concentration of 30% (w/w). The solution was well mixed and allowed to stand for 2–3 hours at room temperature to provide a malleable putty with excellent formability properties.

Example II:

A putty of 20% Pluronic F127 with 420–850 micron cortical allograft bone powder @50%.

519 milligrams of freeze dried cortical allograft bone of particle size of 420–850 microns was mixed into 518 milligrams of a 20% solution of Pluronic F127 in isotonic saline. The bone component is added to achieve a bone concentration of 50%(w/w). The solution was well mixed and allowed to stand for 2–3 hours at room temperature. This provided a putty with poor formability properties.

Example III:

A putty of 20% solution of Pluronic F 108 with 420–850 micron cortical allograft bone powder @50%.

528 milligrams of freeze dried cortical allograft bone of particle size of 420–850 microns was mixed into 522 milligrams of a 20% solution of Pluronic F108 in isotonic saline. The bone component is added to achieve a bone concentration of 50%(w/w). The solution was well mixed and allowed to stand for 2–3 hours at room temperature. This provided a putty with poor formability properties.

Example IV:

A malleable putty of 20% solution of Dextran 40PM with 420–850 micron cortical allograft bone powder @33%.

502 milligrams of freeze dried cortical allograft bone of particle size of 420–850 microns was mixed into 1,024 milligrams of a 20% solution of Dextran 40 PM in isotonic saline. The bone component is added to achieve a bone concentration of 33%(w/w). The solution was well mixed and allowed to stand for 2–3 hours at room temperature. This provided a malleable putty with moderate formability properties.

Example V:

A malleable putty of 20% solution of Pluronic F127 with 100–300 micron cortical allograft bone powder @33%.

503 milligrams of freeze dried cortical allograft bone of particle size of 100–300 microns was mixed into 1,004 milligrams of a 20% solution of Pluronic F127 in isotonic saline. The bone component is added to achieve a bone concentration of 33%(w/w). The solution was well mixed and allowed to stand for 2–3 hours at room temperature. This provided a malleable putty with excellent formability properties.

Example VI:

A malleable putty of 20% solution of Pluronic F108 with 100–300 micron cortical allograft bone powder @33%.

502 milligrams of freeze dried cortical allograft bone of particle size of 100–300 microns was mixed into 1,006 milligrams of a 20% solution of Pluronic F108 in isotonic saline. The bone component is added to achieve a bone concentration of 33%(w/w). The solution was well mixed and allowed to stand for 2–3 hours at room temperature. This provided a malleable putty with excellent formability properties.

Example VII:

A malleable putty of 20% solution of Dextran 40 PM with 100–300 micron cortical allograft bone powder @33%.

502 milligrams of freeze dried cortical allograft bone of particle size of 100–300 microns was mixed into 1,006 milligrams of a 20% solution of Dextran 40 PM in isotonic saline. The bone component is added to achieve a bone concentration of 33%(w/w). The solution was well mixed and allowed to stand for 2–3 hours at room temperature. This provided a malleable putty with excellent formability properties.

Example VIII:

A malleable putty of 3% solution hyaluronic acid with 100–300 micron cortical allograft bone powder @33%.

720 milligrams of freeze dried cortical allograft bone of particle size of 100–300 microns was mixed into 1,402 milligrams of a 3% solution of sodium hyaluronate in isotonic saline. The bone component is added to achieve a bone concentration of 33%(w/w). The solution was well mixed and allowed to stand for 2–3 hours at room temperature. This provided a malleable putty with excellent formability properties.

Example IX:

A malleable putty of 1% solution hyaluronic acid with 250–420 micron cortical allograft bone powder @40%.

605 milligrams of freeze dried cortical allograft bone of particle size of 250–420 microns was mixed into 906 milligrams of a 1% solution of sodium hyaluronate in isotonic saline. The bone component was added to achieve a bone concentration of 40% (w/w). The solution was well mixed and allowed to stand for 2–3 hours at room temperature. This provided a malleable putty with poor formability properties.

Example X:

A malleable putty of 3% solution chitosan with 100–300 micron cortical allograft bone powder @33%.

507 milligrams of freeze dried cortical allograft bone of particle size of 100–300 microns was mixed into 1,002 milligrams of a 3% solution of chitosan in isotonic saline. The bone component is added to achieve a bone concentration of 33%(w/w). The solution was well mixed and allowed to stand for 2–3 hours at room temperature. This provided a malleable putty with good formability properties.

Example XI:

A malleable putty of 3% solution chitosan with 420–850 micron cortical allograft bone powder @33%.

518 milligrams of freeze dried cortical allograft bone of particle size of 420–850 microns was mixed into 1,038 milligrams of a 3% solution of chitosan in isotonic saline. The bone component is added to achieve a bone concentration of 33%(w/w). The solution was well mixed and allowed to stand for 2–3 hours at room temperature. This provided a malleable putty with good formability properties.

Example XII:

A malleable putty of 3% solution chitosan with 420–850 micron cortical allograft bone powder @50%.

518 milligrams of freeze dried cortical allograft bone of particle size of 420–850 microns was mixed into 522 milligrams of a 3% solution of chitosan in isotonic saline. The bone component is added to achieve a bone concentration of 50%(w/w). The solution was well mixed and allowed to stand for 2–3 hours at room temperature. This provided a malleable putty with poor formability properties.

Example XII:

A malleable putty of 3% solution chitosan with 100–300 micron cortical allograft bone powder @50%.

518 milligrams of freeze dried cortical allograft bone of particle size of 100–300 microns was mixed into 522 milligrams of a 3% solution of chitosan in isotonic saline. The bone component is added to achieve a bone concentration of 50%(w/w). The solution was well mixed and allowed to stand for 2–3 hours at room temperature. This provided a malleable putty with poor formability properties.

Example XIV:

A flowable gel of 250–420 micron particle size cortical allograft bone granules in a 1% solution of Hyaluronic Acid at a 25% (w/w) of bone content.

503 milligrams of allograft freeze dried cortical bone was mixed into 1,502 milligrams of a 1% solution of sodium hyaluronate in isotonic saline. The solution was well mixed and allowed to stand at room temperature to provide a flowable gel.

Example XV:

A flowable gel of 250–420 micron particle size cortical allograft granules in a 1% solution of hyaluronic acid at a 30% (w/w) of bone content.

501 milligrams of allograft freeze dried cortical bone was mixed into 1,167 milligrams of a 1% solution of sodium hyaluronate in isotonic saline. The bone component is added to achieve a bone concentration of 30%(w/w). The solution was well mixed and allowed to stand for 2–3 hours at room temperature. This provided a flowable gel.

Example XVI:

A flowable gel of 420–850 micron particle size cortical allograft granules in a 1% solution of hyaluronic acid at a 25% (w/w) of bone content.

501 milligrams of allograft freeze dried cortical bone was mixed into 1,501 milligrams of a 1% solution of sodium hyaluronate in isotonic saline. The bone component is added to achieve a bone concentration of 25%(w/w). The solution was well mixed and allowed to stand for 2–3 hours at room temperature. This provided a flowable gel.

Example XVII:

A flowable gel of 420–850 micron particle size cortical allograft granules in a 1% solution of hyaluronic acid at a 30% (w/w) of bone content.

500 milligrams of allograft freeze dried cortical bone was mixed into 1,166 milligrams of a 1% solution of sodium hyaluronate in isotonic saline. The bone component is added to achieve a bone concentration of 30%(w/w). The solution was well mixed and allowed to stand for 2–3 hours at room temperature. This provided a flowable gel.

The following Table I sets forth the above noted examples in comparative form:

In summation, it can been seen from Table I that:

A flowable gel can be made up of about 25–30% bone powder (particle size in a range of 250–850 microns) mixed into a high molecular weight hydrogel carried in solution, such as 1% sodium hyaluronate (Examples XIV, XV, XVI, XVII).

A putty with good formability can be made up of about 30–40% of bone powder (particle size in a range of 100–850 microns) mixed into a hydrogel solution, such as a 2–3% sodium hyaluronate or 3% chitosan or a 20% Pluronic (Examples I, V, VI, VII, VIII, X, and XI).

Several examples of (II, III, IX, XII and XIII) of test results are included which did not produce either a successful flowable gel or putty. These show the limits of the concentrations of the respective examples. Particle sizes below about 100 microns will absorb too quickly.

In order to preclude oxidation degradation and loss of viscosity the composition should be mixed and packaged in an oxygen free environment. The mixing of the demineralized bone powder into hydrogel solution is undertaken in an enclosed sterile glove chamber with an oxygen free environment such as in a nitrogen, argon or other inert gas filled chamber. The mixed malleable bone composition is then placed in a sterile container such as an impervious syringe barrel or vial, sealed and placed in a sterile sealed package which is filled with an inert gas or vacuum sealed.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

TABLE I

| Example # | Ref # | Carrier Solution | Bone mg/ Carrier mg | Bone % | Particle Size (micron) | Comments | Putty/Gel |
|---|---|---|---|---|---|---|---|
| I | 4.2 | 2% HA | 502 mg/1170 mg | 30 | 250–420 | good | putty: excellent formability |
| II | 1b | 20% Pluronic F127 | 519 mg/515 mg | 50 | 420–850 | too dry, too grainy | putty: poor formability |
| III | 2b | 20% Pluronic F108 | 528 mg/522 mg | 50 | 420–850 | too dry, too grainy | putty: poor formability |
| IV | 3b3 | 20% Dextran 40 PM | 502 mg/1024 mg | 33 | 420–850 | good, grainy; moderate packing capacity | putty: moderate formability |
| V | 1a1 | 20% Pluronic F127 | 503 mg/1004 mg | 33 | 100–360 | best; good, keeps shape; very good packing, moldability, sticky | putty: excellent formability |
| VI | 2a2 | 20% Pluronic F108 | 502 mg/1006 mg | 33 | 100–300 | best; good but slightly wet, good packing, sticky | putty: excellent formability |
| VII | 3a3 | 20% Dextran 40 PM | 502 mg/1006 mg | 33 | 100–300 | best | putty: excellent formability |
| VIII | 7a7 | 3% HA | 720 mg/1402 mg | 33 | 100–300 | good consistency, slightly sticky and slightly dry | putty: excellent formability |
| IX | 2-6 | 1% HA | 605 mg/906 mg | 40 | 250–420 | too grainy, very dry | putty: poor formability |
| X | 5a5 | 3% Chitosan | 507 mg/1002 mg | 33 | 100–300 | best | putty: good formability |
| XI | 5b5 | 3% Chitosan | 518 mg/1038 mg | 33 | 420–850 | good/grainy; too dry, packs well, too large granules | putty: good formability |
| XII | 5b | 3% Chitosan | 518 mg/522 mg | 50 | 420–850 | too dry, too grainy | putty: poor formability |
| XIII | 5a | 3% Chitosan | 518 mg/522 mg | 50 | 100–300 | too dry, won't hold shape; too dry, not puttylike, too dry, no packing | putty: poor formability |
| XIV | 5-1 | 1% HA | 503 mg/1502 mg | 25 | 250–420 | Wet, still good consistency and formability, very moderately grainy | flowable gel |
| XV | 5-2 | 1% HA | 501 mg/1167 mg | 30 | 250–420 | drier than 5-1, reasonable formability, much grainier | flowable gel |
| XVI | 5-4 | 1% HA | 501 mg/1501 mg | 25 | 420–850 | wet, grainy, not formable, may be flowable | flowable gel |
| XVII | 5-5 | 1% HA | 500 mg/1166 mg | 30 | 420–850 | wet, formable, grainy | flowable gel |

What we claim is:

1. A sterile malleable bone composition for application to a bone defect site to promote new bone growth at the site comprising a mixture of demineralized [osteogenic] *osteoinductive* bone powder with a particle size ranging from about 100 to about 850 microns in a carrier, the bone powder ranging from about 25 to about 35% of the weight of the composition, the carrier is selected from the group consisting of sodium hyaluronate[,] *and* chitosan [and N,O-carboxymethylchitosan] in water solution having a high molecular weight ranging from five hundred thousand to three million Daltons and ranging from about 1.0% to about 3.0% by weight of the carrier solution.

2. A malleable bone composition as claimed in claim 1 wherein said mixture includes bone morphogenic proteins in excess of the amount naturally occurring in allergenic bone.

3. A malleable bone composition as claimed in claim 1 including the addition of a calcium salt to the carrier.

4. A malleable bone composition as claimed in claim 1 wherein the balance of the carrier formulation contains a sodium phosphate buffer and having a pH of about 7.2.

5. A malleable bone composition as claimed in claim 1 wherein said bone powder is cortical allograft bone powder.

6. A malleable bone composition as claimed in claim 1 wherein said bone powder is corticocancellous allograft bone powder.

7. A sterile malleable bone putty composition for application to a bone defect site to promote new bone growth at the site which comprises a new bone growth inducing mixture of demineralized lyophilized allograft bone powder with a particle size ranging from about 100 to about 850 microns in a hyaluronic acid water carrier, the hyaluronic acid component ranging from above 1.0% to about 3% of the carrier solution and having a molecular weight of at least $10^6$ Daltons and a viscosity ranging from 6,000 to about 275,000 cps, the bone content of the carrier ranging in weight from about 25% to about 35% total weight of the composition.

8. A malleable bone putty composition as claimed in claim 7 including the addition of a calcium salt to the hyaluronic acid carrier.

9. A malleable bone putty composition as claimed in claim 8 wherein said calcium salt is calcium chloride.

10. A malleable bone putty composition as claimed in claim 8 wherein said calcium salt is calcium sulfate.

11. A malleable bone putty composition as claimed in claim 8 wherein said calcium salt is calcium phosphate.

12. A malleable bone putty composition as claimed in claim 8 wherein said calcium salt is calcium hydroxyapatite.

13. A malleable bone putty composition as claimed in claim 7 wherein said carrier has a 2–3% hyaluronic acid concentration with the balance of the carrier formulation comprising saline water.

14. A malleable bone putty composition as claimed in claim 7 wherein said carrier has a 2–3% hyaluronic acid concentration with the balance of the carrier formulation comprising sterile water.

15. A malleable bone putty composition as claimed in claim 7 wherein said hydrogel carrier has a 2–3% hyaluronic acid concentration with the balance of the carrier formulation contains a sodium phosphate buffer with a pH of about 7.2, said buffer attracting calcium and concentrating same at the bone defect site.

16. A malleable bone putty composition as claimed in claim 7 wherein said carrier includes BMP in excess of the amount naturally occurring in allergenic bone.

17. A malleable bone putty composition as claimed in claim 7 wherein said bone powder is cortical allograft bone powder.

18. A malleable bone putty composition as claimed in claim 7 wherein said bone powder is corticocancellous.

19. A malleable bone putty composition as claimed in claim 7 including antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin.

20. A malleable bone putty composition as claimed in claim 7 including vitamins.

21. A malleable bone putty composition as claimed in claim 7 including enzymes such as collagenase, peptidases and oxidases.

22. A malleable bone putty composition for application to a bone defect site to promote new bone growth at the site comprising a new bone growth inducing demineralized lyophilized allograft bone powder with a particle size ranging from about 100 to about 420 microns in a high molecular weight sodium hyaluronate and water carrier, the bone content of the composition ranging from about 30% to about 35% by weight and the high molecular weight sodium hyaluronate component ranges from about 2% to about 3% of the carrier and has a molecular weight greater than one million Daltons.

[23. A sterile malleable bone putty composition for application to a bone defect site to promote new bone growth at the site which comprises a new bone growth inducing compound of demineralized lyophilized allograft bone powder with a particle size ranging from about 100 to about 420 microns in a N,O-carboxymethylchitosan water carrier solution, the N,O-carboxymethylchitosan component ranging from about 1.0% to about 3% of the carrier weight and having a molecular weight ranging from $2.0\times10^6$–$3.0\times10^6$ Daltons.]

24. A malleable bone putty composition for application to a bone defect site to promote new bone growth at the site which comprises a new bone growth inducing demineralized lyophilized allograft bone powder with a particle size ranging from about 100 to about 850 microns in a high molecular weight chitosan water carrier solution with the bone content of the putty composition ranging from about 30% to about 35% and the chitosan component comprising about 3% of the carrier solution with the chitosan having a molecular weight ranging from about $1.0\times10^3$ to $3.0\times10^5$ Daltons.

25. A malleable bone putty composition as claimed in claim 24 wherein the carrier formulation includes a sodium phosphate buffer of about pH 7.2.

26. A malleable bone putty composition as claimed in claim 24 wherein said carrier solution includes saline water.

27. A malleable bone putty composition as claimed in claim 24 wherein said carrier solution includes sterile water.

28. A malleable bone gel composition for application to a bone defect site to promote new bone growth at the site which comprises a new bone growth inducing amount of demineralized lyophilized allograft bone powder with a particle size ranging from about 250 to about 850 microns in a high molecular weight hyaluronic acid in water carrier with the hyaluronic acid component comprising about 1% of the carrier and having a molecular weight over $1.0\times10^6$ Daltons, the bone powder content of the compositions ranging from about 25% to about 30%.

29. A malleable bone gel composition for application to a bone defect site to promote new bone growth at the site comprising a new bone growth inducing amount of demineralized lyophilized allograft bone powder with a particle size ranging from about 250 to about 420 microns mixed in a high molecular weight hyaluronic acid water solution carrier with the hyaluronic acid component being present in the amount of about 1% of the carrier and having a viscosity of about 1,800 to 13,000 cps, the bone powder amount content of the composition ranging from about 25% to about 30% by weight.

* * * * *